(12) United States Patent
Ferree

(10) Patent No.: US 6,514,255 B1
(45) Date of Patent: Feb. 4, 2003

(54) SUBLAMINAR SPINAL FIXATION APPARATUS

(76) Inventor: Bret Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 09/513,128

(22) Filed: Feb. 25, 2000

(51) Int. Cl.[7] .................................................. A61F 2/30
(52) U.S. Cl. .......................... 606/61; 606/76; 606/103
(58) Field of Search ............................. 606/61, 60, 74, 606/86, 103, 76

(56) References Cited

U.S. PATENT DOCUMENTS

| | | | |
|---|---|---|---|
| 4,557,259 A | * 12/1985 | Wu | |
| 4,643,178 A | * 2/1987 | Nastri et al. | |
| 5,413,576 A | 5/1995 | Rivard | 606/61 |
| 5,476,465 A | 12/1995 | Preissman | 606/61 |
| 5,501,688 A | * 3/1996 | Whiteside et al. | 606/103 |
| 5,540,689 A | 7/1996 | Sanders et al. | 606/61 |
| 5,782,831 A | 7/1998 | Sherman et al. | 606/61 |
| 5,928,237 A | * 7/1999 | Farris et al. | 606/74 |
| 5,964,769 A | 10/1999 | Wagner et al. | 606/74 |
| 5,993,452 A | * 11/1999 | Vandewalle | 606/74 |
| 6,086,590 A | * 7/2000 | Margulies et al. | 606/61 |

OTHER PUBLICATIONS

US 5,772,633, 6/1998, Whiteside et al. (withdrawn)*

* cited by examiner

Primary Examiner—Jeffrey A. Smith
(74) Attorney, Agent, or Firm—Gifford, Krass, Groh, Sprinkle, Anderson & Citkowski, PC

(57) ABSTRACT

Devices, instrumentation, and surgical techniques are described for a more structured coupling of lamina to an alignment rod. A body having an aperture formed therethrough to receive the rod includes a mechanism to lock the body in place once a desired position and two or more holes to receive a cable wrapped around a lamina to be stabilized. A sleeve may also be provided over the cable where it wraps around the lamina to distribute the force of the cable against the bone to prevent damage. The mechanism to lock the body in place preferably includes a threaded fastener having an exposed proximal end for tightening and a distal end that bears against the rod. The body may be unitary, or provided in sections, one with the aperture and the other with the cable receiving holes, and with the two sections being rotatable relative to one another. At least one of the cable-receiving holes may also be flared or ring-shaped to facilitate a range of motion to avoid cable fatigue. The invention also provides instrumentation facilitating sublaminar cable fixation, comprising a tool having a proximal end with a handle and a distal end. The distal end terminates in a curved, cannulated section between two cable-receiving holes, the length of the curved section and the distance between the holes being such that the proximal end may be positioned under a lamina to feed the cable therearound.

11 Claims, 2 Drawing Sheets

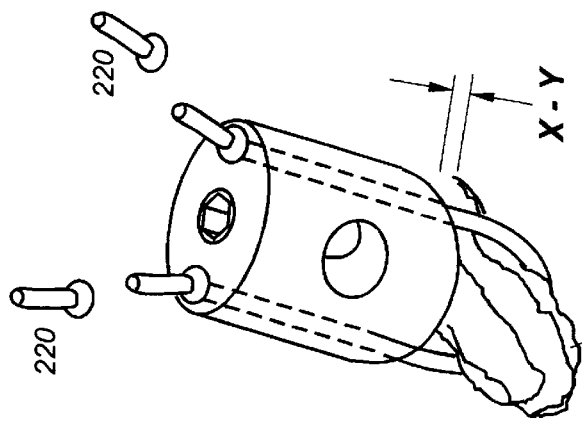
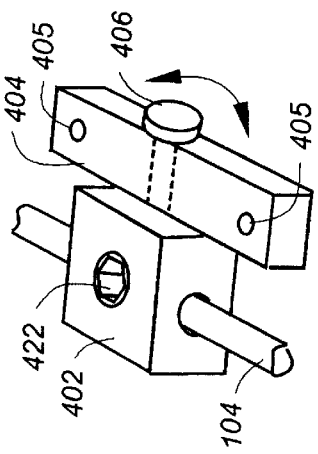
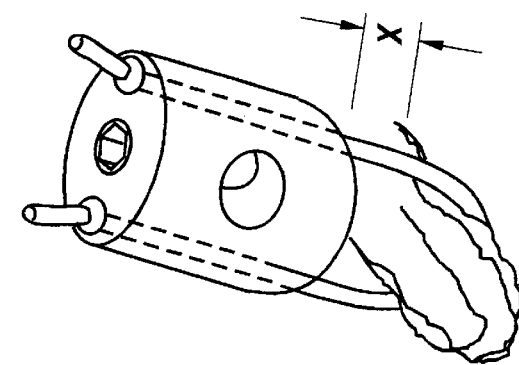
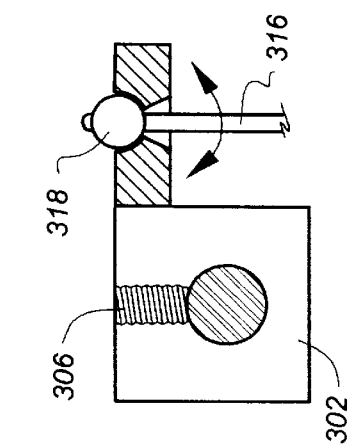
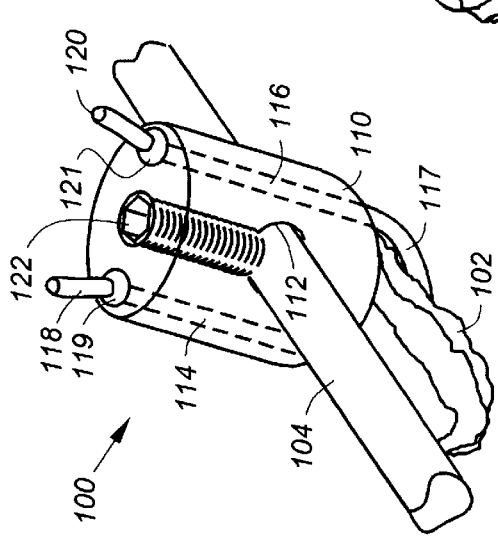
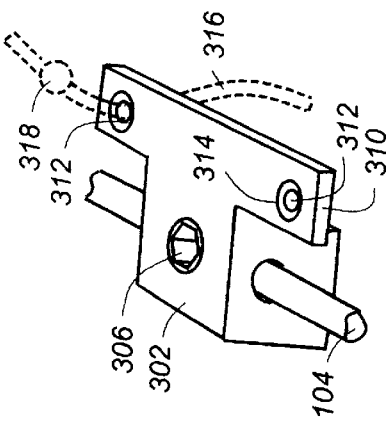

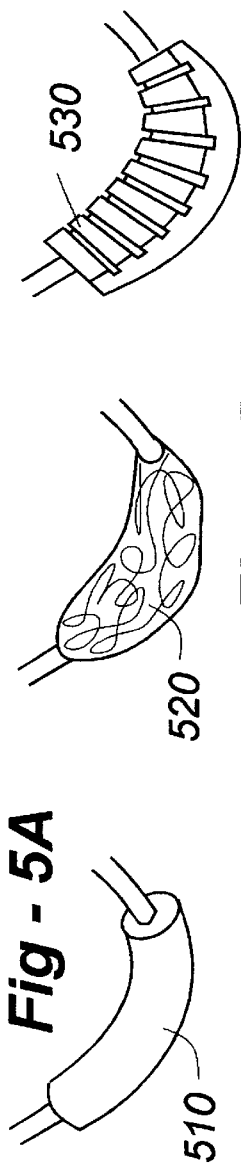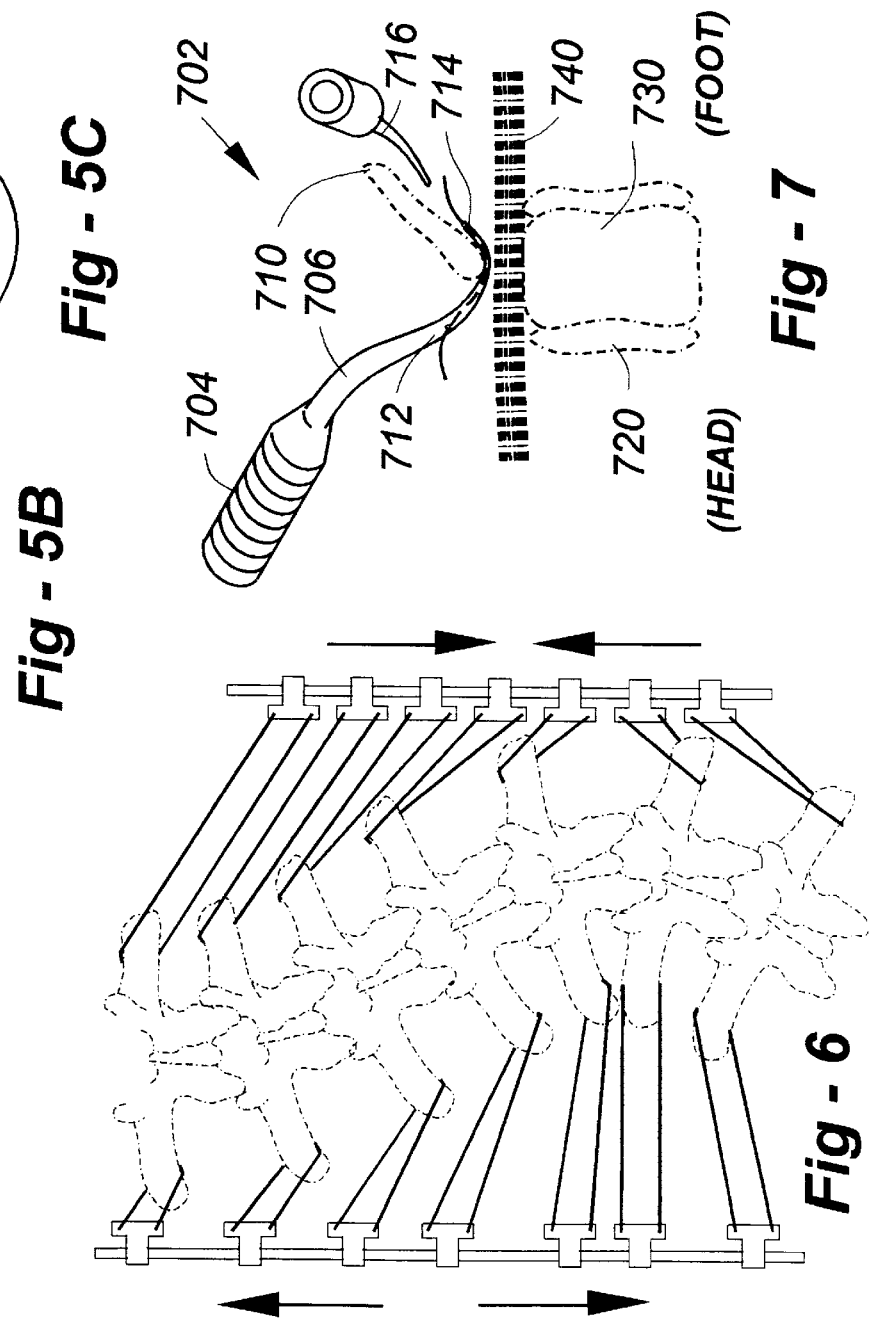

SUBLAMINAR SPINAL FIXATION APPARATUS

FIELD OF THE INVENTION

The present invention relates generally to spinal surgery and, more particularly, to improved spinal fixation devices and methods of using the same.

BACKGROUND OF THE INVENTION

The human spine exhibits some degree of curvature at different levels to facilitate normal physiologic function. Correction may be required when this curvature deviates substantially. A common problem is lateral deviation of the spine, commonly termed scoliosis.

As discussed in U.S. Pat. No. 5,540,689, the first successful internal fixation method for surgically treating scoliosis used the Harrington instrumentation system. According to this technique, a rigid rod with hooks at each end is implanted adjacent the concave side of the scoliotic spine. The spine is manually straightened to a desired extent and a distraction rod is used to maintain the correction by exerting vertical forces at each end. The rod commonly has a ratcheted end over which hooks are slidably mounted and locked in place. To accommodate lordosis, a compression rod is sometimes placed on the convex side of the scoliotic spine.

The Harrington instrumentation system has been used successfully for some time, but because the distraction rod is fixed to the spine in only two places, failure at either end causes the entire system to fail. An alternative treatment has since evolved which takes advantage of segmented fixation. In this method, a rod is fixed to the spine at multiple points by means of a sublaminar wires which run underneath the lamina of the vertebra and around the rod. The use of multiple fixation sites enhances stability and reduces the need for additional post-operative bracing.

Sublaminar fixation utilizing current devices has two primary weaknesses, however. First, the wires are simply wrapped around the rod, resulting in a rod to cable junction which is not rigid. Second, the thin wires can cut in some instances right through the lamina. Thus, the need remains for a more structured approach to this procedure.

SUMMARY OF THE INVENTION

This invention solves problems associated with existing sublaminar fixation techniques by providing devices, instrumentation, and surgical techniques for a more structured coupling of lamina or other bony spinal structures to an alignment rod.

In terms of apparatus, the invention provides a body having an aperture formed therethrough to receive the rod, a mechanism to lock the body in place once a desired position is established along the rod, and two or more holes through the body to receive a cable wrapped around at least a portion of each vertebra to be stabilized. A sleeve may also be provided over the cable where it wraps around the structure to distribute the force of the cable against the bone to prevent damage.

In a preferred embodiment, the mechanism to lock the body in place includes a threaded fastener having an exposed proximal end for tightening and a distal end that bears against the rod. The body may be unitary, or provided in sections, one with the aperture and the other with the cable receiving holes, and with the two sections being rotatable relative to one another. The orientation of the cable-receiving holes may be varied relative to the aperture for the rod for convenient cable connection to different spinal structures such as the lamina and/or spinous process. At least one of the cable-receiving holes may also be flared or ring-shaped to facilitate a range of motion to avoid cable fatigue.

The invention also provides instrumentation facilitating sublaminar cable fixation, comprising a tool having a proximal end with a handle and a distal end. The distal end terminates in a curved, cannulated section between two cable-receiving holes, the length of the curved section and the distance between the holes being such that the proximal end may be positioned under a lamina or other bony structure to feed the cable therearound.

BRIEF DESCRIPTION OF THE DRAWINGS

FIG. 1 is a perspective view of a rod-mounted cable holding sublaminar fixation device according to the invention;

FIG. 2A is the first drawing of a sequence, showing how cables may be progressively tensioned using the inventions;

FIG. 2B shows a subsequent step relative to FIG. 2A, wherein a lamina is pulled closer to a inventive device and recrimped, in this case;

FIG. 3A is a drawing which shows a device according to the invention having an alternative cable holder, wherein a cup-shape recess or ring is used in conjunction with a ball-shaped cable end for a greater range of motion;

FIG. 3B is a drawing which illustrates the improved range of motion made possible by the device according to FIG. 3A;

FIG. 4 is a drawing which shows how separate rod-holding and cable-holding sections may be rotatably coupled to one another;

FIG. 5A is a drawing of a covering in the form of a resilient sleeve to distribute forces and protect laminar bone;

FIG. 5B is an alternative covering using wire mesh;

FIG. 5C is yet a further force-distributing sleeve using a corregated surface to facilitate bending;

FIG. 6 is a posterior view of a spine with scoliosis used to show how devices according to the invention may be longitudinally positioned to accommodate distraction and compression; and FIG. 7 is a drawing of a tool according to the invention used to dress cables around and behind a lamina for use with the devices described herein.

DETAILED DESCRIPTION OF THE DRAWINGS

According to one aspect, the invention provides a device to which a rod and cabling attached, resulting in a versatile, more reliable and stable interconnection. A preferred embodiment of such a device is depicted generally at 100 in FIG. 1. The device includes a body 110 having an aperture 112 to receive a rod 104. In addition, holes has 116 through the body accept a cable 117 which is dressed around a spinal structure such as lamina 102. Although the following description concentrates on laminar attachment, it will be appreciated that the invention may be configured for convenient attachment to other spinal structures, preferably bony protrusions, such as the spinal process. In such a case, the connectors for wires placed through the spinous processes may use cable-receiving holes which are perpendicular (or at other angles) relative to the orientation of the holes shown in the figures.

The aperture 112 is preferably such that the body may slide on the rod until being locked into place with some form of tightening mechanism. In the preferred embodiment this takes the form of a manual fastener such as set screw 122 having an exposed proximal end for tightening and a distal end that bears against the rod. The cable may be tightened using existing techniques, after which ends 118 and 120 are crimped at points 119 and 121 to provide a rigid securement of lamina 102 to rod 104.

FIGS. 2A and 2B illustrate the way in which a lamina 102 may be progressively pulled toward the body of the device and, hence, the rod (not shown) by increasing cable tension. In FIG. 2A, the lamina 102 is located at a distance x from the device whereas, in FIG. 2B, the distance is lessened to x-y through cable pulling. With conventional cables the ends may be re-crimped with the excess 220 being trimmed away. Such as approach is particularly beneficial in correcting deformities through repeated tightening, as discussed further below.

FIG. 3 is a drawing which depicts an alternative cable-rod connector according to the invention. In this case, a main body portion 302 includes a side portion 310 having cable-receiving holes 312. A fastener such as set screw 306 would again be used to lock the body onto the rod 104. Preferably, holes 312 are formed with cup-shaped recesses 314 or are simply ring-shaped. This enables cables 316 having ball-shaped crimps 318 to cooperate with the recess or ring holder to allow for a large range of cable movement without the cable impinging on surrounding structures. Acute cable angles are also preferably avoided to decrease the risk of cable failure.

FIG. 4 illustrates yet a further alternative embodiment of the invention, wherein a side portion 404 is rotatably attached to a main body portion 402 which is locked onto the rod 104 using fastener 422. Preferably side portion 404 is joined to the body 402 through a post 406 enabling the component 404 to rotate for an enhanced conformity to patient physiology when the cables (not shown) are tightened. Although the cable-receiving holes 405 are not shown with cup-shaped recesses as discussed with reference to FIG. 3, such a feature is applicable to this and indeed all of the embodiments described herein.

The invention also contemplates optional sleeves for increasing the surface area of the cable against the lamina, thereby distributing the force to prevent damage to the bone. Various cable coverings may be used for this purpose according to the invention, including sleeve 510 of resilient material in FIG. 5A, wire mesh bundle 520 in FIG. 5B, or a flexible pad with ribs, as shown in FIG. 5C. It will be appreciated that these examples are not exhaustive, and that other elements which increase cable surface area would be anticipated by the invention.

The rigid connection between the cables and the rods according to the invention allows the application of longitudinal forces by the cables. The loose rod cable connection in existing devices does not allow for the application of such forces. As shown in FIG. 6, the ability to apply these forces enables the surgeon to better correct spinal deformities such as scoliosis.

The invention further anticipates apparatus and surgical techniques passing wires or cables under the lamina in a safer manner. FIG. 7 is a cut-away view of the spine as seen from the side showing such instrumentation and techniques. From this perspective, the spinal cord is shown at 740, along with a vertebra 730 and disc 720. A tool 702 according to the invention includes a handle 704 and a distal end 706 which is curved to fit under a lamina 710, as shown. The curved end 706 is also cannulated, having a first hole 712 and a second hole 714 through which the cable is inserted. A small endoscope 716 may be used to observe the cable pass under the lamina. Alternatively, a suture could be used to pull the cable, or magnets could be used to attract the cable, or any combination of such techniques. A preferred endoscope would be manipulated so as to turn at the distal end, as with devices used in other specialties such as ear, nose and throat surgery. A strong light would be directed under the opposite side of the lamina to direct the surgeon.

In summary, the devices and procedures described herein offer several advantages over prior-art apparatus and methods. First, the use of a rigid cable/rod connection allows less spinal movement which, in turn, should lead to a higher rate of fusion. The rigid cable/rod connection also allows for the application of longitudinal forces, which are important in the correction of spinal deformities. The use of provisional and progressive cable tensioning is also important in this respect. The ball-and-socket/swivel cable fixation system offers a versatile range of cable motion to help avoid cable wear and fatigue. The sleeves and alternatives covers used to increase the surface area help prevent the cables from cutting through the lamina or other structures. The tools and techniques for directing cables provide a more controlled approach to the procedure.

I claim:

1. A sublaminar fixation device for use with a rod and a fixation element to align multiple vertebra having bony structures, the device comprising:

a body having an aperture formed therethrough to receive the rod;

a mechanism to lock the body in place once a desired position is established along the rod; and two holes extending through the body to receive the fixation element, each hole being aligned along a separate axis, the axes being spaced apart on either side of the aperture.

2. The sublaminar fixation device of claim 1, further comprising a sleeve configured for placement over the fixation element where it wraps around the bony structure.

3. The instrumentation of claim 2, wherein the fixation element is a wire, cable or band.

4. The sublaminar fixation device of claim 1, wherein the mechanism to lock the body in place includes a threaded fastener having an exposed proximal end for tightening and a distal end that bears against the rod.

5. The sublaminar fixation device of claim 1, wherein:

the body includes two sections, one with the aperture and the other with the holes to receive the fixation element; and the two sections rotate relative to one another.

6. The sublaminar fixation device of claim 1, wherein:

one end of the fixation element is widened; and at least one of the holes through the body is flared to engage with the widened end of the element to facilitate a range of element motion.

7. The sublaminar fixation device of claim 6, wherein:

the wider end of the element is ball-shaped; and the flared hole is cup- or ring-shaped.

8. The instrumentation of claim 7, wherein the fixation element is a wire, cable or band.

9. The instrumentation of claim 6, wherein the fixation element is a wire, cable or band.

10. The sublaminar fixation device of claim 1, wherein:

the holes are oriented to wrap the cable around a lamina or spinous process.

11. The instrumentation of claim 1, wherein the fixation element is a wire, cable or band.

* * * * *